United States Patent [19]

Otani et al.

[11] Patent Number: 5,049,074
[45] Date of Patent: Sep. 17, 1991

[54] DENTAL IMPLANT

[75] Inventors: Sugio Otani, 2010-2, Kurokawa, Hishi-machi, Kiryu-shi, Gumma-ken; Sadakatsu Yanagisawa, 3-34-407, Mita 2-chome, Minato-ku, Tokyo; Kunio Niijima, No. 563, Kamiko-machi, Omiya-shi, Saitama-ken; Kazusi Matuura, Tokyo; Hirosi Matino, Yokohama; Tooru Fuse, Tokyo, all of Japan

[73] Assignees: Sugio Otani, Kiryu; Sadakatsu Yanagisawa, Tokyo; Kunio Niijima, Omiya; Mitsubishi Kasei Corporation; Research Development Corporation of Japan, both of Tokyo, all of Japan

[21] Appl. No.: 500,924

[22] Filed: Mar. 29, 1990

[30] Foreign Application Priority Data

Mar. 29, 1989 [JP] Japan .................................. 1-77696
Mar. 29, 1989 [JP] Japan .................................. 1-77697

[51] Int. Cl.⁵ .............................................. A61C 8/00
[52] U.S. Cl. .................................. 433/173; 433/201.1
[58] Field of Search .................... 433/201.1, 173, 174, 433/175, 176; 623/16

[56] References Cited

U.S. PATENT DOCUMENTS

| 3,934,347 | 1/1976 | Lash et al. | 433/173 |
| 3,981,736 | 9/1976 | Broemer et al. | 623/16 |
| 4,051,598 | 10/1977 | Sneer | 433/173 |
| 4,424,037 | 1/1984 | Ogino et al. | 433/201.1 |
| 4,457,984 | 7/1984 | Otani et al. | 433/201.1 |
| 4,599,085 | 7/1986 | Riess et al. | 433/173 |
| 4,648,842 | 3/1987 | Grundei | 433/175 |
| 4,818,559 | 4/1989 | Hama et al. | 433/173 |

FOREIGN PATENT DOCUMENTS

| 0211676 | 2/1987 | European Pat. Off. | 433/173 |
| 1042834 | 11/1958 | Fed. Rep. of Germany | 433/173 |
| 0249632 | 9/1987 | Fed. Rep. of Germany | 433/173 |
| 2092891 | 8/1982 | United Kingdom . | |

Primary Examiner—John J. Wilson
Attorney, Agent, or Firm—Oblon, Spivak, McClelland, Maier & Neustadt

[57] ABSTRACT

A dental implant comprising a core material and a porous layer formed on the core material, wherein at least a part of the core material coated by the porous layer has a non-circular cross-sectional shape so as not to rotate relative to the porous layer.

7 Claims, 2 Drawing Sheets

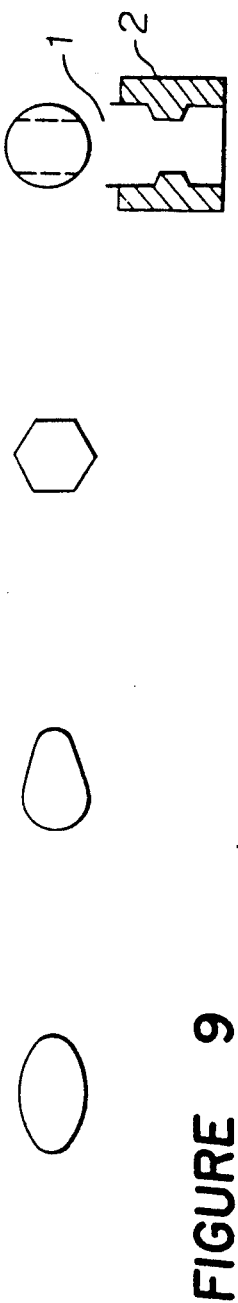
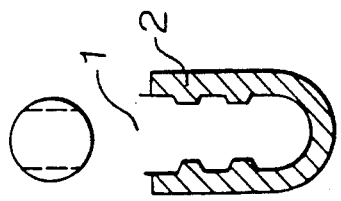

DENTAL IMPLANT

The present invention relates to a dental implant.

When a tooth is lost for some reason, the cavity formed by the missing tooth will be gradually filled by a new bone, but the peripheral portion undergoes bone atrophy since no mastication pressure is exerted thereto, and eventually the jaw bone tends to be slender. A dental implant is intended to supplement such a missing tooth and to provide the same mastication function as a natural tooth. The dental implant is required to be compatible with the bone tissue and free from toxicity and yet have sufficient strength. As such a dental implant, those made of a metal material such as stainless steel, a cobalt-chromium alloy, titanium or a titanium alloy, a ceramic material such as alumina, hydroxyapatite or bioglass, or a carbon material, have been developed. Some of them have already been practically used.

Particularly, alumina or a carbon material which is a biologically inactive material, is chemically stable and safe with little deterioration of the mechanical properties in a living body and has good compatibility with a living body.

When a dental implant made of such a material, is to be implanted in a bone tissue, it is known to employ a method wherein the portion of the dental implant which is in contact with the living body, is provided with a threaded structure as a means to increase the bonding strength between the living body and the dental implant, and the dental implant is thereby physically fixed, or a method wherein a ceramic porous layer or a carbon porous layer is used to permit the proliferation of the bone tissue so that the dental implant is thereby fixed (e.g. Japanese Examined Utility Model Publication No. 34731/1981). In particular, some of the present inventors have developed a dental implant having a special porous layer utilizing an excellent affinity of carbon to a living body (Japanese Examined Patent Publication No. 9859/1986). It has been confirmed that when such a dental implant is employed, the bone tissue penetrates and proliferates in the porous layer to establish firm bonding between the living body and the dental implant. For the bonding of the core material and the porous layer in such an artificial tooth material, it has been proposed to employ welding in the case where both materials are made of metal, or bonding with a glass layer or a mechanical fixing method by means of a threaded structure of the core material in the case where both materials are made of ceramics (Japanese Examined Utility Model Publication No. 34731/1981).

However, in the conventional dental implants, no mechanical fixing method other than the threaded structure has been used for the bonding of the core material and the porous layer, whereby a deterioration in the interface bonding strength between the core material and the porous layer, interfacial peeling, loosening or rotation of the core material and eventually a possibility of falling off of the core material, are likely due to the shock at the time of embedding the dental implant in the jaw bone or due to repeated chewing impacts over a long period of time after the implantation of the dental implant.

Even if the dental implant has a threaded structure, such a structure does not serve to prevent the rotation of the core material.

Further, with the conventional dental implants, no interlocking connection to the living body is available immediately after the implantation, whereby the dental implants are likely to move, which tend to lead to failures of the dental treatment.

On the other hand, a dental implant having a threaded structure may be excellent in the initial fixing, but has a difficulty that it tends to be loosened from the living body during its use for a long period of time.

Further, some of dental implants made of alumina have a porous threaded structure. However, the elasticity of alumina itself is as high as at least 10 times the elasticity of the bone tissue, and the stress is likely to be locally concentrated, and thus it is likely to lead to loosening of the dental implant for a long run.

Under these circumstances, the present inventors have conducted extensive researches to solve such conventional problems and as a result, have found it possible to solve such problems by improving the previously developed dental implant having the special carbon porous layer so that it has a special outer shape and the core material has a special shape. The present invention has been accomplished on the basis of this discovery.

It is an object of the present invention to provide a dental implant whereby the treatment will be easy, a desired function will be provided immediately after the treatment, a stabilized fixed state can be maintained for a long period of time, and which is free from falling off or rotation of the core material.

Such an object can readily be accomplished by a dental implant of the present invention which comprises a core material and a porous layer formed on the core material, wherein at least a part of the core material coated by the porous layer has a non-circular cross-sectional shape so as not to rotate relative to the porous layer.

In the accompanying drawings:

FIGS. 1 to 8 illustrate different embodiments of the non-circular cross-sectional shape of the core material of the dental implant of the present invention.

FIG. 9 illustrates the dental implant used in Example 1.

Figure 10:
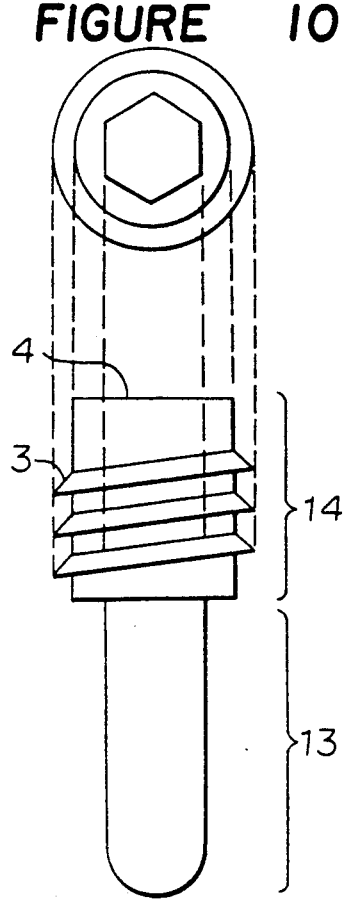
FIGS. 10, 11 and 12 illustrate embodiments of the core material, the crown base and the cap of the dental implant of the present invention.

Now, the present invention will be described in detail. The dental implant of the present invention comprises a core material and a porous layer. More particularly, the porous layer is formed on the surface of the core material. Here, the shape of the core material is a rod shape. Its material is not particularly limited. However, usually various carbon fiber-reinforced carbon materials, sintered carbon or glass-like carbon material, or a metal such as platinum, titanium, tantalum or tungsten, or ceramics such as alumina, zirconia, calcium phosphate, titania or biologically active glass, may be mentioned. It is preferred to use a carbon fiber-reinforced carbon material, titanium or alumina, which is biologically inactive and has high strength.

The porous layer is not particularly restricted so long as it can be formed on the above-mentioned core material, and when the dental implant is implanted in a living body, the vital tissue can penetrate into pores of the porous layer, and a firmly bonded tissue can be formed by the steric structure of the pores and the penetrated vital tissue, and the bonded tissue can undergo calcification to form a bone tissue. Specifically, a porous layer of alumina or a carbon-type porous layer obtained by depositing pyrolytic carbon on a non-woven fabric such as carbon fiber, may be mentioned. As the porous layer made of alumina, the one disclosed in Japanese Examined Utility Model Publication No. 34731/1981 can be employed. For example, an organic material (e.g. a spherical product or chopped fibers of PVA or polyethylene) is mixed to e.g. $Al_2O_3$ powder, and then the organic material is burned off and evaporated until the sintering or semi-sintering temperature of ceramics is reached, to obtain a porous layer having continuous pores. above core material. When the woven fabric, non-woven fabric, felt or paper is employed, such a material is cut into a proper size and attached by means of an organic adhesive, as the case requires, and if necessary, it is further wound and fixed by long fibers. When chopped strands are employed, an organic adhesive is coated on the necessary portion of the surface of the substrate, and chopped strands are sprinkled and fixed thereto. Then, pyrolytic carbon is precipitated and integrated to the material thereby obtained (hereinafter referred to as a piling carbon material). This pyrolytic carbon treatment is preferably conducted in such a manner that pyrolytic carbon is precipitated under such a condition that the temperature of the substrate is from 600° to 2300° C., preferably from 700° to 1100° C., with a negative temperature gradient from the substrate to the surface, whereby an excellent carbon porous layer is formed.

Namely, the above-mentioned conditions are suitable so that the core material and the fiber material on the surface are firmly bonded to each other, and at the same time a porous layer having a pore distribution such that the interior of the fiber material i.e. the core material side, is most dense and the porosity gradually increases towards the external surface layer.

The dental implant of the present invention comprises such a porous layer and the core material. It is important in the present invention that at least a part of the core material has a non-circular cross-sectional shape, and the core material will not rotate. Here, the non-circular cross section is not particularly limited so long as it is a shape whereby the core material will not rotate. Specifically, it may be any one of the shapes as shown in FIGS. 1 to 9. Accordingly, it is required to be not a threaded structure. The core material may have such a non-circular cross sectional shape in its entirety or a part thereof. The porous layer of the present invention is formed on such a core material, so that the interfacial peeling and rotation between the core material and the porous layer will be prevented.

Preferably, the core material has a shape as shown in FIG. 8 (1: pore material, 2: porous layer) so that it is effective not only against the rotation but also against the shearing in the longitudinal direction of the core material and the porous layer. More preferably, in addition to the non-circular cross section, a surface roughness with the maximum height ($R_{max}$) of at least 10 μm is provided on the surface of the core material by e.g. blast treatment. The blast treatment may be conducted, for example, in such a manner that an abrasive sand such as alumina (#100) or SiC is blasted against the surface of the core material by means of compressed air to form the roughness on the surface of the core material.

In the present invention, the core material of the dental implant has a non-circular cross section, whereby the shock to the jaw bone at the time of implanting the dental implant and the shear stress at the interface between the core material and the porous layer due to the chewing for a long period of time after the implantation of the dental implant, can be reduced. Thus, substantial effects against the rotation or falling off of the core material can be expected.

Further, in the present invention, the porous layer has a porosity (void rate) of at least 10% and preferably has an average porosity of from 30 to 40%. Typically, for example, it has a structure in which fibers are randomly piled and mutually firmly bonded. The pores thus formed preferably have pore sizes of at least 100 μm, preferably at least 200 μm, and such pore sizes preferably gradually decrease towards the interior.

In general, a dental implant is required to have adequate elasticity and strength to be durable against substantial impacts or force. To such requirements, the dental implant of the present invention provides an extremely effective performance by virtue of the presence of the porous layer, the vapor phase pyrolytic carbon precipitated thereon and the threaded structure provided to the surface of the dental implant at a position where the surface of the dental implant and the bone tissue are in contact. Namely, the dental implant is covered by the vapor phase pyrolytic carbon and is extremely strong by itself, and when implanted in a living body, the vital tissue penetrates into pores of the porous layer, and the penetrated connective tissue undergoes calcification and is converted to a bone tissue by the bone-inducing action of the carbon and the steric structure of pores. Thus, the carbon fibers and the vital tissue will form a mutually intertwined double network structure, whereby the dental implant is firmly bonded and fixed to the living body.

Further, the threaded portion is located at a position which is in contact with the bone tissue without having the above porous layer. In other words, the dental implant of the present invention is bonded and fixed to the bone tissue by means of the threaded portion and the porous portion. By the threaded portion, the initial fixing after the implantation of the dental implant is ensured, and by the porous layer, semi-permanent bonding and fixing will be ensured by the calcification and conversion to the bone tissue of the periphery of the dental implant.

If necessary, the dental implant after the formation of the porous layer is shaped into the final form by means of e.g. a grinder. When the dental implant of the present invention is to be used for the dental treatment, it is subjected to sterilizing treatment and then implanted into a living body. In order to facilitate the penetration of the vital tissue into the porous layer, a biologically active ceramics such as apatite or bioglass, or a cell-proliferation promoting substance such as a bone-inducing factor, may be impregnated or coated to the porous layer. To apply a ceramics, a method such as dipping in a slurry having the ceramics dispersed therein, flame spraying or CVD (chemical vapor deposition) may be employed. The application of the cell-proliferation promoting substance may be conducted by the method disclosed in Japanese Examined Patent Publication No. 125260/1988.

Further, in order to improve the adhesion to the gingival epithelium and the vital tissue in contact with the threaded portion, the surface of the core material may be coated with a biologically active ceramics such as apatite or bioglass. As the coating technique, flame spraying or glass firing may be employed.

When the dental implant of the present invention is used for the dental treatment, the dental implant and the crown base may be unified or may be separable. In the unified case, a crown is mounted after the dental implant is sufficiently bonded and fixed upon expiration of from 2 to 3 months after the implantation in the bone tissue.

In the separable case, the center portion of the core material is made hollow, and a cap is preferably provided to the hollow portion to prevent the penetration of the vital tissue. If necessary for the fixing of the cap, an adhesive such as a bone cement may be employed. The material for the cap is not limited to a polymer, a metal, a ceramics or carbon so long as it is stable in the living body. However, a cap made of a polymer with high precision requires no adhesive. Therefore, a polymer such as a polysulfone resin is preferred. After placing the cap, the epithelium is once sutured. Upon expiration of from 2 to 3 months, the epithelium is again incised, and the cap is withdrawn, and a crown base is inserted into the hole 4 (FIG. 10) of the tooth root and fixed with a bone cement. And then the epithelium is again sutured. A few days later, a crown is attached to the crown base so that the mastication pressure will be exerted. The dental implant may be implanted in either method. However, the latter method is preferred, since the consistency of the period until the vital tissue sufficiently penetrates, is better in the latter method.

Now, the present invention will be described in further detail with reference to Examples. However, it should be understood that the present invention is by no means restricted to such specific Examples.

EXAMPLE 1

In a titanium metal having a diameter of 2 mm, a groove of 150 $\mu$m was formed as shown in FIG. 9 to obtain a core material 1 having a non-circular cross section. To this core material, a non-woven fabric of carbon fibers having a thickness of 0.5 mm was wound, and vapor phase pyrolytic carbon was deposited under the following conditions by means of a high frequency induction heating furnace:

Starting material organic substance: Dichloroethylene
Carrier gas: Argon
Pyrolytic temperature: 900° C.
Deposition period: 1.5 hours.

The deposited sample was subjected to surface treatment to obtain a cylindrical dental implant having a porous layer 2 having a thickness of 1300 $\mu$m with a porosity gradient and a pore size gradient from the surface of the porous layer towards the core material side.

A core material having a circular cross section of Comparative Example 1 was subjected to the same treatment to obtain a cylindrical dental implant (not shown).

Then, the bottom portion of each cylindrical dental implant was removed, and a punching test of the core material and the porous layer was conducted simulating the shearing force at the time of embedding the dental implant to the jaw bone.

The results are shown in Table 1.

TABLE 1

|  | Shape of the core material | Surface roughness | Punching load | State of fracture |
| --- | --- | --- | --- | --- |
| Example 1 | non-circular cross section | 10 $\mu$m | 100 kg | Fracture of the porous layer |
| Comparative Example 1 | Circular cross section | 10 $\mu$m | 30 kg | Interfacial fracture |

With the core material having a non-circular cross section (Example 1), the dental implant was durable until the porous layer broke. Whereas, with the circular cross section (Comparative Example 1), the interface broke. From the foregoing, it is evident that with the non-circular cross section, the shearing stress between the pore material and the porous layer can be reduced over the circular cross section, whereby substantial effects against the rotation or falling off of the pore material can be expected.

EXAMPLE 2

Figure 11:
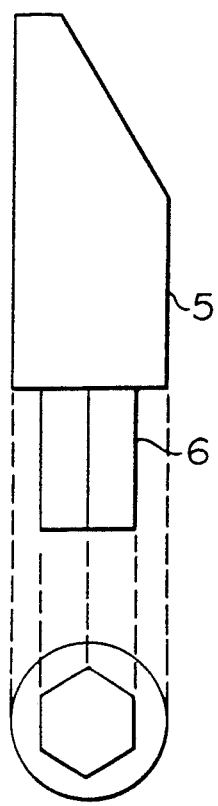
Figure 12:
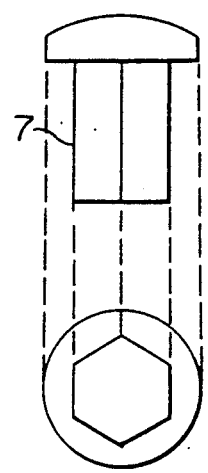

In FIG. 10, a dental implant of the present invention is shown. A titanium rod was ground to form a neck portion 14 having a diameter of 4 mm and a length of 4 mm and a porous layer base portion 13 having a diameter of 2 mm and a length of 8 mm. Three threads 3 with a pitch of 0.8 mm were provided from 1 mm from the upper end of the neck portion downwardly. Then, a hexagonal hole (a hole 4 for fixing a crown base) was formed in the neck portion to receive a crown base 5 (FIG. 11). This Example shows a case where the dental implant and the crown base 5 are separable. However, they may be formed integrally (6: connecting portion to the hole 4).

Then, a felt of carbon fibers was wound on the porous layer base portion, and carbon was deposited among the carbon fibers under the following conditions by means of a high frequency induction heater, to form a porous layer.

CVD conditions

Starting material: Dichloroethylene
Carrier gas: Argon
Temperature: 900° C.
Time: 90 minutes After shaping by a grinder, the porous layer had a surface pore size of 200 $\mu$m and a porosity of 60% and a thickness of about 1 mm, whereby the porosity and the pore diameter were found to increase towards the surface.

The dental implant thus prepared was screwed into the lower jaw bone of a monkey having a body weight of about 4 kg while threading the bone by the threaded portion. A cap made of a polysulfone resin (FIG. 3, 7: connecting portion to the hole 4) was inserted to the hole 4 of the dental implant, and the the epithelium was sutured. After expiration of 2 months, the epithelium was incised again, and the resin cap was withdrawn from the dental implant, and the crown base 5 was inserted into the hole 4 of the dental implant and fixed with a bone cement. Then, the epithelium was again sutured. A few days later, a crown 9 was attached to the crown base 5 so that the mastication pressure would be exerted.

Figure 13:
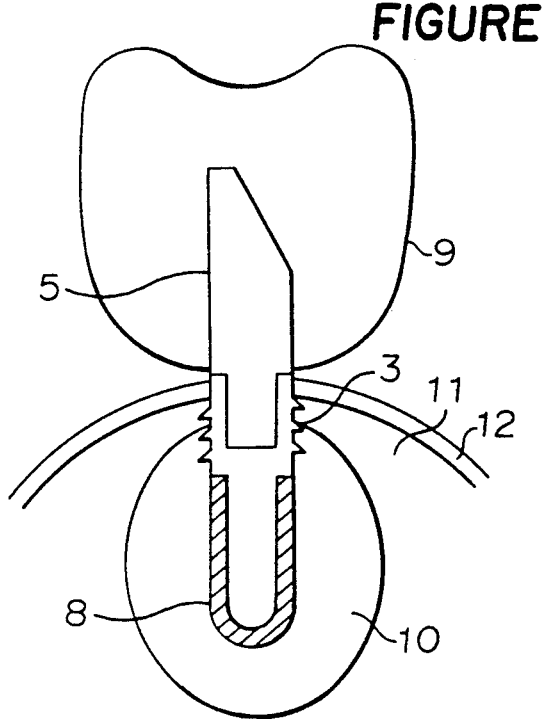
FIG. 13 is a cross-sectional view illustrating the dental implant of the present invention after mounting the crown.
Figure 14:
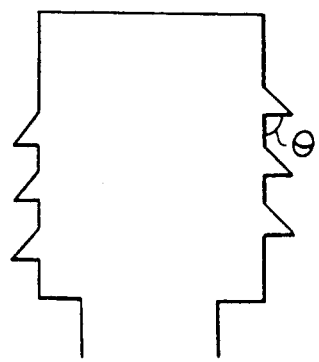
FIG. 14 is a cross-sectional view illustrating the threaded portion of the dental implant.

In FIG. 13, reference numeral 8 indicates the porous layer, numeral 10 indicates a sponge bone, numeral 11 indicates a dense bone, and numeral 12 indicates the gingival epithelium.

Upon expiration of 3 months, the treatment was confirmed to be successful.

According to the present invention, at least a part of the core material of the dental implant having a porous layer is made to have a non-circular cross section, whereby the shearing stress at the interface between the core material and the porous layer can be reduced, and substantial effects against the rotation or falling off of the core material can be expected, and a constant use of the dental implant for a long period of time after the implantation will be possible.

Further, since it has a porous layer, the vital tissue penetrates into pores, and due to the steric structure of pores, the penetrated connective tissue will be calcified and converted to a bone tissue, whereby a dental implant firmly bonded and fixed to the living body is obtainable.

Furthermore, by the threaded structure provided at a portion of the core material, the dental implant and the jaw bone are mechanical bonded immediately after the implantation, whereby the movement of the implanted dental implant will be prevented until the interlocking with the living body is established. Thus, the success rate in the dental operation will be increased, and the period until the crown can be attached, will be shortened.

What is claimed is:

1. A dental implant comprising a core material and a porous layer formed on the core material, wherein at least a part of the core material coated by the porous layer has a non-circular cross-sectional shape, said porous layer covering the non-circular cross-sectional area of said core material so as not to rotate relative to the porous layer, and wherein said porous layer has a thickness of at least 0.1 mm, and the pore size is at least 100 $\mu$m, at the surface of the porous layer and gradually decreases from the surface towards the core material side.

2. The dental implant according to claim 1, wherein the porous layer has a porosity of at least 10%.

3. The dental implant according to claim 1, wherein the porous layer is composed essentially of a carbon material.

4. The dental implant according to claim 1, wherein the portion of the dental implant, which is in contact with the bone tissue, comprises a threaded portion and said porous layer.

5. The dental implant according to claim 1, wherein the core material is made of an electrically conductive carbon or metal material.

6. The dental implant according to claim 1, wherein the porous layer has a porosity of from 30 to 40%.

7. The dental implant according to claim 1, wherein the core material has a surface roughness $R_{max}$ of at least 10 $\mu$m formed by blast treatment.

* * * * *